United States Patent
Fotinos

(10) Patent No.: US 7,087,240 B1
(45) Date of Patent: Aug. 8, 2006

(54) DEVICE AND METHOD FOR THE TREATMENT OF ERECTILE DYSFUNCTION

(75) Inventor: Spiros Fotinos, Athens (GR)

(73) Assignee: Lavipharm Laboratories Inc., Piscataway, NJ (US)

( * ) Notice: Subject to any disclaimer, the term of this patent is extended or adjusted under 35 U.S.C. 154(b) by 0 days.

(21) Appl. No.: 09/340,338

(22) Filed: Jun. 25, 1999

Related U.S. Application Data

(60) Provisional application No. 60/090,674, filed on Jun. 25, 1998.

(51) Int. Cl.
*A61K 9/70* (2006.01)
*A61F 13/00* (2006.01)

(52) U.S. Cl. ............... 424/449; 424/400; 424/484; 424/486

(58) Field of Classification Search ............ 424/448, 424/449, 484, 443, 444, 445, 447, 400, 486
See application file for complete search history.

(56) References Cited

U.S. PATENT DOCUMENTS

| | | | | |
|---|---|---|---|---|
| 4,696,821 A | * | 9/1987 | Belsole | 424/448 |
| 4,812,313 A | | 3/1989 | Gale | 424/448 |
| 4,829,991 A | | 5/1989 | Boeck | 128/79 |
| 4,867,982 A | | 9/1989 | Campbell et al. | 424/449 |
| 4,954,344 A | | 9/1990 | Gale | 424/448 |
| 5,152,997 A | | 10/1992 | Ebert et al. | 424/449 |
| 5,242,391 A | | 9/1993 | Place et al. | 604/60 |
| 5,302,395 A | | 4/1994 | Ebert et al. | 424/449 |
| 5,333,621 A | | 8/1994 | Denzer | 128/844 |
| 5,420,197 A | | 5/1995 | Lorenz et al. | |
| 5,474,535 A | | 12/1995 | Place et al. | 604/60 |
| 5,480,648 A | | 1/1996 | Wendel et al. | 424/448 |
| 5,492,911 A | | 2/1996 | Stief | 514/252 |
| 5,576,290 A | | 11/1996 | Hadley | 514/11 |
| 5,658,936 A | | 8/1997 | Kifor et al. | 514/381 |
| 5,698,589 A | | 12/1997 | Allen | 514/509 |
| 5,741,511 A | | 4/1998 | Lee et al. | 424/449 |
| 5,773,020 A | * | 6/1998 | Place et al. | 424/426 |
| 5,842,039 A | | 11/1998 | Hanaway et al. | 395/831 |
| 5,914,118 A | * | 6/1999 | Yamamura et al. | 424/402 |
| 6,001,380 A | * | 12/1999 | Smith et al. | 424/449 |
| 6,007,836 A | * | 12/1999 | Denzer | 424/449 |
| 6,589,990 B1 | * | 7/2003 | Kanakaris et al. | 514/573 |

FOREIGN PATENT DOCUMENTS

| | | |
|---|---|---|
| EP | 0 249 194 | 12/1987 |
| EP | 0 266 968 A | 5/1988 |
| EP | 0459 377 A2 | 12/1991 |
| FR | 2710649 * | 4/1995 |
| FR | 2710649 A1 * | 4/1995 |
| FR | 2 748 658 A | 11/1997 |
| WO | WO94/28902 | 12/1994 |

OTHER PUBLICATIONS

Webster's New World Dictionary of American English Ed. Neufeldt and Guralnik Simon & Shuster, Inc New York p. 1156 1988.*
Webster's New World Dictionary of American English Ed. Neufeldt and Guralnik Simon & Shuster, Inc New York p. 1156 1988.*
Kligman et al., *Arch. Derm.* 88, 702, (1963).
Franz, J., *J. Invest. Derm.* 64:90-105 (1975).
U.S. Appl. No. 09/398,846, Fotinos.

* cited by examiner

*Primary Examiner*—Thurman K. Page
*Assistant Examiner*—Pili A. Hawes
(74) *Attorney, Agent, or Firm*—Dechert LLP

(57) ABSTRACT

Devices and methods for treatment of erectile dysfunction and methods of manufacture and of use are provided. The devices include filmogenic material, a therapeutic agent, a permeation enhancer, and other ingredients. An embodiment of the device includes a backing and a release liner.

72 Claims, 1 Drawing Sheet

DEVICE AND METHOD FOR THE TREATMENT OF ERECTILE DYSFUNCTION

RELATED APPLICATION

This application claims priority from provisional application 60/090,674 filed Jun. 25, 1998, which is hereby incorporated by reference herein.

TECHNICAL FIELD

Delivery devices, methods of manufacture and methods of use for noninvasive treatment of erectile dysfunction are provided.

BACKGROUND ART

Erectile dysfunction is considered a common disorder affecting approximately 10% of men of any age. The incidence of this dysfunction, however, increases dramatically with age. By definition, erectile dysfunction is the inability to attain and maintain the erection of the penis a sufficient time to permit satisfactory sexual intercourse. The cause of erectile dysfunction may be of psychogenic, organic, iatrogenic, or hormonal origin. Psychogenic based erectile dysfunction may occur in patients under age 35 due to psychological disorders such as depression, anxiety, stress, performance anxiety etc. Organic based dysfunction may occur in older patients due to a vascular, cavernosal or neurological disease such as atherosclerosis, hypertension, smoking, diabetes, spinal injury, multiple sclerosis etc. Iatrogenic based dysfunction mainly appears after the administration of drugs or the performance of medical/surgical procedures. It has been reported that over 130 drugs can cause erectile dysfunction as a side effect, including for example such drugs as antihypertensives (e.g. β-blockers and diuretics) and hypoglycemics. Hormonal based dysfunction mainly occurs due to changes in testosterone levels or other hormones or chemical messengers.

The cause of impotence commonly determines the treatment of penile erectile dysfunction, with the ultimate goal of recovering sexual activity. Treatment may involve procedures such as psychotherapy, vascular surgery, or prosthetic surgery. Alternatively, therapeutic agents may be selected for pharmacotherapy which can be administered orally, topically, intra-urethrally or injected intracavernously (EP 702555; EP 249194; EP 459377; U.S. Pat. Nos. 5,242,391; 5,474,535; 5,492,911; 5,576,290; 5,658,936; 5,698,589; and 5,842,039). In certain circumstances, specific devices may be used in treatment such as a vacuum cylinder device. The cause of the dysfunction may determine the therapeutic approach of choice.

Where therapeutic agents are used, different routes of administration of the agent to the subject are associated with certain disadvantages. For example, the intra-urethral route of administration may cause side effects for both patient and partner because a portion of the administered drug remains in the urethra and, thus, can be transmitted to the partner during intercourse. The self-injection route during intracaverneous administration has disadvantages associated with lack of spontaneity and unpleasant and sometimes pathological side effects and suffers from a high drop-out rate of the user population. Although oral administration is a convenient and attractive approach of therapy, this approach is open to abuse by patients without erectile dysfunction, but who would try an oral formulation for improving performance. The topical route relying on a gel, cream, or ointment lacks dose precision at the site of application, namely the penis skin. Transdermal delivery methods have been utilized for the systemic treatment of certain disorders as in U.S. Pat. Nos. 5,152,997; 4,812,313; 4,954,344; and 5,302,395. Several trials to optimize drug delivery to the penis by the transdermal route leading to successful sexual intercourse have resulted in developing a variety of transdermal drug delivery systems. There are however problems associated with these systems relating to the change in the surface texture of the penis and the implications of friction of penis against vagina.

Where attempts have been made to employ transdermal delivery devices for the treatment of erectile dysfunction, a rather complicated vasodilator delivery system has been developed (U.S. Pat. No. 5,333,621) which is complex in design and inconvenient to use. The system consists of three or two adhesive layers, which are adhered inside a condom. Upon use, the three layer patch is adhered to the penis skin after applying pressure to the condom.

Another transdermal delivery device for the treatment of male impotence is described in U.S. Pat. No. 5,741,511. The device is in the form of a cylinder matrix type or a multi-reservoir patch applied to the glans penis. Even in this case, to obtain the maximum of the desired effect the patch has to be accompanied by a support and rings attached to the penis. After achieving enough erection, the patch and support are removed while the rings remain during the intercourse. This device is unpleasant and inconvenient for both the patient and his partner.

Still another transdermal delivery device (patch) containing prostaglandin for the treatment of any pathological condition (e.g. peripheral arterial occlusive disease) is described in U.S. Pat. No. 5,480,648. The patch described in '648 consists of a pressure sensitive adhesive containing the active and other additives, laminated onto a backing film. However, the drug release profile of this patch disclosed long term delivery which is unsuited for the treatment of erectile dysfunction because an effective dose of an active agent is required over a short period of time prior to intercourse so as to provide a positive response (rigid tumescence of penis).

Therefore, there is a need to develop a system and method for the treatment of erectile dysfunction that is simple, safe, convenient and painless to use, but not open to abuse and that delivers an effective "therapeutic dose" to the penis over a short period of time and is applied directly to the penis surface without using any additional support, and eventually enables the patient to achieve normal sexual activity.

SUMMARY OF THE INVENTION

Accordingly, the invention in a first embodiment is a delivery device for treatment of erectile dysfunction in a patient, comprising a patch formed from a filmogenic polymer, and having an effective dose of a therapeutic agent suitable for reversing erectile dysfunction. This embodiment comprises further at least one additive contained within the patch, wherein the at least one additive is selected from the group consisting of a stabilizer, a solubilizer, an enhancer and a plasticizer. The therapeutic agent is in one embodiment a prostaglandin, preferably prostaglandin E1. In another embodiment, the therapeutic agent is selected from the group consisting of: a vasodilator, a smooth muscle relaxant, an anti-depressant, a parasympathetic stimulator, a renin-angiotensin system inhibitor, a local anesthetic, an α-blocker, and a calcium channel blocker. The device can comprise further at least an additional therapeutic agent. For example, the at least one additional therapeutic agent can be selected from the group consisting of: a prostaglandin, a testosterone, a yohimbine, a pentoxifylline, a trazodone, an apomorphine, a phentolamine, a sildenafil, aminoxidil, a misoprostol, a papaverine, a nitroglycerin, a phentolamine, a moxisylyte, a linsidomine, a linear peptide, a cyclic peptide, and a pyridylguanidine compound.

In the embodiment of the delivery device, the enhancer is at least one selected from the group consisting of a glycolipid, a non-esterified fatty acid, an aliphatic alcohol, a fatty acid ester of an aliphatic alcohol, a cyclohexanol, a cyclohexanol derivative, a fatty acid ester of glycerol, a glycol, an aliphatic alcohol ether of a glycol, and a surfactant. In a preferred embodiment of the device, the filmogenic polymer is polyvinyl pyrrolidone, the therapeutic agent is prostaglandin E1, the enhancer is Eutanol G16S, and the plasticizer is PEG 400. Further, the filmogenic material is present in an amount of 5 to 100%, the therapeutic agent is present in an amount of 0.1 to 20% w/w, the enhancer is present in an amount of 0.01 to 15%, and the plasticizer is present in an amount of 1 to 70%, each on a weight basis. In another embodiment of the delivery device, the filmogenic material is present in an amount of 5 to 50%, the therapeutic agent is present in an amount of 1 to 10%, the permeation enhancer is present in an amount of 1 to 10%, and the plasticizer is present in an amount of 3 to 50%. A preferred embodiment has polyvinyl pyrrolidone present in an amount that is 40 to 45%, has prostaglandin E1 present in an amount that is 5 to 10%, has Eutanol G16S present in an amount that is 1 to 4%, and has PEG 400 present in an amount that is 40 to 50%.

In another aspect of the delivery device delivery is transdermal. In a different embodiment delivery is transmucosal. The effective dose is released into the subject within one hour.

In another embodiment, the invention is a method of treating erectile dysfunction, comprising: selecting a patch formed from a filmogenic polymer and comprising one or more therapeutic agents selected from the group consisting of a vasodilator, a smooth muscle relaxant, an anti-depressant, a parasympathetic stimulator, a renin-angiotensin system inhibitor, a local anesthetic, an α-blocker, and a calcium channel blocker; and delivering the therapeutic agent to the penile surface over an effective period of time. In forming the patch, the therapeutic agent is selected from the group consisting of a prostaglandin, a testosterone, a yohimbine, a pentoxifylline, a trazodone, an apomorphine, a phentolamine, a sildenafil, a minoxidil, a misoprostol, a papaverine, a nitroglycerin, a phentolamine, a moxisylyte, a linsidomine, a linear peptide, a cyclic peptide, and a pyridylguanidine compound. The therapeutic agent is present in a range of 0.1–15%, on a dry weight basis. In one aspect of this embodiment, the patch further comprises adding a plasticizer, for example, the plasticizer is present in an amount that is 30 to 60% on a dry weight basis, and delivering the therapeutic agent to the penile surface does not require pre-wetting. In another aspect of this embodiment, the plasticizer is present in an amount that is less than 30% on a dry weight basis, and delivering the therapeutic agent to the penile surface has the additional step of pre-wetting the surface. Preferably, the plasticizer is a polyethylene glycol (PEG), even more preferably, the PEG is PEG 400. In this embodiment, the filmogenic polymer can be a synthetic polymer, for example, the synthetic polymer is polyvinyl pyrrolidone. Further, the filmogenic polymer can be a plant protein, for example, a prolamine, preferably a gliadin or a mixture of gliadins. In these embodiments, the effective period of time is 5–100 minutes, for example, the effective period of time is 30–60 minutes. In these embodiments, the penile surface is selected from the group consisting of the shaft and the glans.

Yet another embodiment of the invention is method of preparation of a flexible disk for treatment of erectile dysfunction, comprising: preparing a composition having prostaglandin E1, Eutanol G16S, PVP, and PEG 400; and forming the composition to have a backing and a release layer. Preferably, the method of preparing the composition includes adding prostaglandin E1 in an amount that is 5 to 10%, adding Eutanol G16S in an amount that is 1 to 5%, adding polyvinyl alcohol pyrrolidone in an amount that is 40 to 50%, and adding PEG 400 in an amount that is 40 to 50%, each on a dry weight basis.

DESCRIPTION OF THE SPECIFIC EMBODIMENTS

Figure 1:
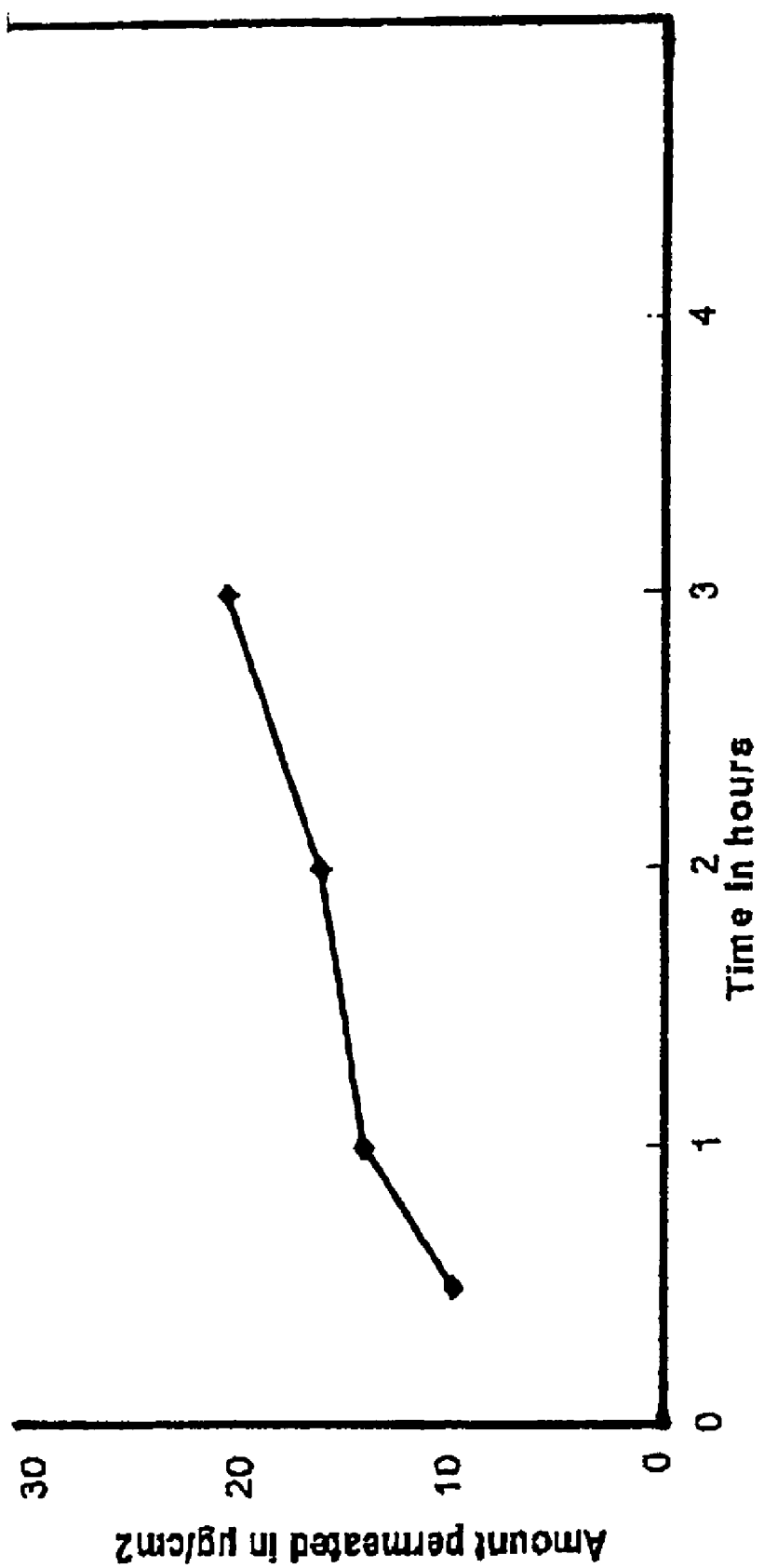
FIG. 1 is a graph showing cumulative permeation of prostaglandin per unit area of stratum corneum as a function of time, in response to administration of the formulation of Example 9.

In accordance with an embodiment of the invention, a biodegradable system in the form of a flexible patch is provided which may be applied directly to the surface of the penis, for example, the penis shaft or the glans. The flexible patch may include an effective dose of a therapeutic agent for the treatment of erectile dysfunction and further may include a carrier for the delivery of the therapeutic agent. In a preferred embodiment, the patch is biodegradable. The flexible patch includes a backing material and a release liner, which is removed prior to application to the penile skin. Formulations of Examples 1–6 and 9 are used to provide a flexible device which is manufactured with a backing and a release liner. Flexibility is contributed by the presence of a plasticizer, for example PEG 400, as a substantial percentage of the formulation of these Examples, for example, PEG 400 is present in an amount that is 30–60% on a dry weight basis, preferably 40–50%, even more preferably 44–48% of the formulation on a dry weight basis.

According to an embodiment of the present invention, the patch can be made of materials known in the art to possess filmogenic properties. The filmogenic materials can preferably be any of synthetic origin, such as polyvinyl pyrrolidone (PVP) or a PVP derivative or another pressure-sensitive adhesive; or the materials can be of semi-synthetic origin such as any of different cellulose derivatives. The filmogenic materials can be of natural origin, such as a polymer from an animal, for example chitin or chitosan from a crustacean exoskeleton, or from a plant, such as a gum, for example, xanthan gum, karaya gum, or a plant resin, for example mastic (for example from *Pistachia lentiscus* var. Chios), or a plant protein such as from wheat or corn, such as a prolamine protein. The prolamine protein can be a zein from maise, a hordein from barley, or a gliadin from wheat. The filmogenic plant protein polymer can be a mixture of proteins, for example, a mixture of wheat gliadins.

In one embodiment, the patch is flexible and contains PVP at a concentration of less than 50%, in which embodiment the PVP is a pressure-sensitive adhesive. In another embodiment, the patch is rigid and requires application to a wet surface, in which embodiment PVP at a higher concentration, for example 90–95%, is a filmogenic material.

In an embodiment of the invention, the patch is rigid and does not require supporting means distinct from the patch, i.e., does not require a backing or a release liner. An embodiment of the invention provides a method of treating male impotence, the method including applying the drug-containing patch to the surface of the penis with pre-wetting the area with a liquid, for example, with water, or an aqueous solution, or a glycol, or any liquid capable both of wetting the patch and of not causing discomfort to the user. A formulation of this embodiment is shown in Example 7, in which the filmogenic synthetic polymer PVP is present in a high amount (91%), and PEG is present as a minor component (3% on a dry weight basis), and in Example 8, in which the filmogenic natural plant protein gliadin is present in a high amount (93.30%), and polysorbate monooleate is present at a low amount (5.00%).

Other additives can be incorporated into the patch to optimize its physicochemical and mechanical properties. The additives may include stabilizers, solubilizers, enhancers, and plasticizers. Permeation enhancers for transmucosal (via the glans) or for transdermal (via the shaft) delivery can be employed for improving the absorption of therapeutic agents through the penis surface to the corpora cavernosa. These may include but are not limited to: glycolipids, fatty acids, aliphatic alcohols, cyclohexanols and their derivatives, esters of glycerol with fatty acids, glycols and ethers of glycols with aliphatic alcohols, surfactants and other compounds known by one of ordinary skill in the art of transdermal and transmucosal drug delivery. Examples of skin permeation enhancers for use in the invention include a glycolipid mixture of plant origin, linoleic acid, polyethylene glycol ether of lauryl alcohol (Lipocol-12), L-menthol, hexyldecyl stearate (Eutanol G16S), polysorbate monooleate, isopropyl myristate, and glycerol monooleate.

The term "transdermal" as used herein and in the claims means a route of delivery of one or more therapeutic agents across the epithelial layer of a patient, including across the stratum corneum comprising dead differentiated epithelial cells that have produced a dry keratinized layer. The term "transmucosal" as used herein shall mean a route of delivery of one or more therapeutic agents across a mucosal epithelial layer. A mucosal epithelial layer is found in an oral (buccal) cavity and in the vaginal cavity of a patient, and in an uncircumsized male, beneath the foreskin of the penis on the glans. Transmucosal and transdermal drug deliverery systems are described in "Transdermal and Topical Drug Delivery Systems," Ed. Ghosh, T. et al. (Buffalo Grove, Ill.: Interpharm Press, Inc., 1997), which describes the higher permeability of mucosal tissue.

An embodiment of the invention which is a rigid patch is suitable for application to the penis shaft or to the glans, for transdermal or transmucosal delivery, respectively, of a therapeutic agent or combination of agents. A user of the rigid patch can in certain circumstances apply the device to the glans without requiring a pre-wetting step. Further, as the higher permeability of mucosal tissue results in the transmucosal route of delivery having more efficient and rapid uptake of a therapeutic agent, a formulation specific for transmucosal delivery can contain decreased amounts of each of the therapeutic agent and the permeation enhancer, compared to a formulation specific for transdermal delivery via the shaft. Alternatively, a user of the rigid patch can shorten the period of application of the patch to the surface of the penis if a transmucosal route, rather than a transdermal route of delivery is chosen, so that a single formulation for both routes can be employed.

Therapeutic agents incorporated in a disk of the invention can include any drug known in the art for the treatment of erectile dysfunction, alone or in combination, preferably drugs that could be administered topically through the skin of the shaft and/or the glans of the penis, such as vasodilators, smooth muscle relaxants, local anesthetics, α-blockers, and calcium channel blockers.

A therapeutic agent present in the device formulations can include but is not limited to a hormone, for example, a steroid hormone such as testosterone, a peptide hormone, an amine hormone, and a hormone-like eicosanoid such as a prostaglandin, a leukotriene, and a thromboxane. In a preferred embodiment, an effective dose of a peripheral vasodilator such as an eicosanoid, preferably a prostaglandin, more preferably, prostaglandin E1 alone or in combination with other therapeutic agents, may be used. In another preferred embodiment, a combination of prostaglandin E1 with a low concentration of a second vasodilator, exemplified by a venous dilator such as nitroglycerin, may be used.

The term "prostaglandin" refers to a family of compounds originally discovered in seminal fluid and found to cause vasodilation, and contraction or relaxation of uterine smooth muscle. The prostaglandins, leukotrienes, and related compounds are called eicosanoids because they are synthesized by microsomal enzymes from 20-carbon essential fatty acids, e.g., arachidonic acid (Hardman, J. 1996, in *Goodman and Gilmans's: The Pharmacological Basis of Therapeutics*, Ch. 26, 9$^{th}$ Ed., McGraw Hill).

In certain embodiments of the invention, additional therapeutic agents may be included in the patch either singly, or in selected combination with any one or more of the aforementioned or following therapeutic agents: testosterone, yohimbine, pentoxifylline (vasodilator), trazodone (antidepressant) apomorphine (parasympathetic stimulator) phentolamine (vasodilator), sildenafil and other pyrozolopyrimidone derivatives. Other agents include minoxidil, misoprostol, papaverine, nitroglycerin, phentolamine, moxisylyte, linsidomine, linear peptides, cyclic peptides, pyridylguanidine compounds, and renin-angiotensin system inhibitors. These agents may be incorporated into a patch at an effective dose to correct erectile dysfunction of the penis. Using a transdermal or a transmucosal device that is an embodiment of the invention, the patch can accommodate a drug load that is ten- to twenty-fold greater than that used for intracavernosal injection as a treatment for erectile dysfunction.

According to an embodiment of the invention, an effective amount of the active agent is released in a time period that is desirable to obtain a positive response (rigid tumescence of penis) for a satisfactory sexual intercourse, for example, 30 to 60 min after application.

According to a preferred embodiment, the invention provides a biodegradable patch comprising, related to the total weight of the carrier and other ingredients: one or more therapeutic agents for the treatment of erectile dysfunction in an amount of 0.1 to 20% w/w, preferably in an amount of 0.1 to 15% w/w on a dry weight basis, more preferably in an amount of 1 to 10% w/w; one or more skin permeation enhancers in an amount of 0.01 to 15% w/w, preferably of 1 to 10% w/w; one or more filmogenic materials in an amount of 5 to 100% w/w, for example, 5 to 50%, 20–50%, 40–60%, and 70–95% w/w; and one or more plasticizers in an amount of 1 to 70% w/w, preferably 3 to 50% w/w.

According to an embodiment of the invention that is a flexible device and that does not require a pre-wetting step, the patch may be placed during manufacturing between two protective layers, namely backing film and release liner, wherein the latter is removed prior to use. Both backing film and release liner can be made of any suitable material known in the art of transdermal drug delivery. Further, the pressure-sensitive adhesive component in the formulation of the flexible patch may be reduced to obtain comfortable application to and removal from the glans, to obtain rapid transmucosal delivery of the therapeutic agents.

An embodiment of the invention is a delivery device for a therapeutic agent for reversing erectile dysfunction, comprising: a flexible patch, the patch being formed from a filmogenic polymer; and containing an effective dose of a therapeutic agent suitable for reversing erectile dysfunction. Delivery in one embodiment can be by a transdermal route, and in another embodiment by a transmucosal route. The device can comprise further at least one additive contained within the patch, wherein the at least one additive is selected from the group consisting of a stabilizer, a solubilizer, an enhancer and a plasticizer. The enhancer is selected from the group consisting of a glycolipid, a fatty acid for example a non-esterified fatty acid, a fatty acid ester of an aliphatic alcohol, an alcohol, a cyclohexanol, an ester of glycerol with one or more fatty acids, a glycols and an ether of a glycol with an aliphatic alcohol, a surfactant, and other compounds known in the art to be used in the present invention. The therapeutic agent is selected from the group consisting of: a vasodilator, a smooth muscle relaxant, a local anesthetic, an α-blocker, and a calcium channel blocker. With this device, the effective dose is released into the subject within one hour.

Another embodiment of the invention is a method of treating erectile dysfunction, comprising: selecting a patch formed from a filmogenic polymer and comprising an eicosanoid or a mixture of eicosanoids; and delivering the eicosanoid to the penile surface over an effective period of time. Accordingly, the eicosanoid in an embodiment of the invention is a prostaglandin, and the effective period of time is 5–100 minutes, preferably the effective period of time is 30–60 minutes.

Fabrication of a Device

A device of the composition in one embodiment can have a release liner layer placed on the composition layer on a surface opposite to that of the backing support. A device can be provided with a tab for convenient removal of the backing or the release liner or both, that has been sheltered from deposition of the composition. Similarly, a tab on the backing support is provided so the device can be grasped by the user for removal of the device from the skin.

The composition can be applied to a release liner or to a non-porous backing support by a standard coating process, for example, using a rotary doctor blade, slot die, a flat film die, or a laboratory coating unit with integrated dryer, for example, LTSV/LTF, W. Mathis AG, Niederhasli, Zurich, Switzerland CH-8155. A solution or dispersion of the composition in the solvent can be deposited as a film or matrix layer to a sheet of a release liner, dried to remove the solvent, and then covered by application of a sheet of backing support. Alternatively, the device can be produced as a layer of composition deposited on a backing support if the support is nonporous, then can be dried to remove the solvent.

An embodiment of a device comprises a backing support of a nonwoven, nonocclusive film of high moisture vapor transmission. The backing support can impart tensile strength so that the device can be handled easily, and applied and removed without leaving a portion of the composition or device remaining on the skin. The backing support can be nonporous, microporous, or macroporous, such as a woven or a nonwoven composition, and can be occlusive, semiocclusive or nonocclusive to moisture. The nonwoven material is selected from the group consisting of polyethylene, polyolefin, polyurethane, polyester, polypropylene, nylon, cotton, rayon, polyvinyl chloride and a cellulosic fiber.

A release liner can be a material selected from the group consisting of paper, polyester, and polystyrene, and can be coated with a silicon or fluorocarbon based release coating. The release liner is removed from the device prior to applying the composition of the matrix layer to skin of a subject having erectile dysfunction. A release liner material can be MediRelease 2226, a polyester silicone release liner obtained from Bertek Medical Products, St. Albans, Vt.

A method of fabrication of a device can be by application of a composition, for example, as in any of Examples 1–6 and Example 9, to deposit it on the surface of a large sheet of a release liner or a non-porous backing to a desired thickness, drying the matrix layer to the sheet, applying a backing or a release liner to the composition layer, and cutting the sheets in a pattern to produce a device which is an embodiment of the invention. Deposition of a solution or a suspension of the composition to a support substrate, can be, for example, to a release liner continuously supplied by a doctor roll apparatus, reverse roll, gravure, slot die or other suitable method to coat the adhesive onto the substrate.

The flexible device can have a thickness of one to 10 mil (a "mil" is $1/1000$ of an inch), preferably a thickness of 2 to 5 mil, more preferably a thickness of 2.5 mil, even more preferably a thickness of 3.5 mil. The backing support can have a thickness of 0.5 to 10 mil, preferably a thickness of 3 to 5 mil. The release liner can have a thickness of 0.5 to 10 mil, preferably a thickness from 3 to 5 mil. The entire device can have a thickness of 3 to 50 mil, for example, can be 4, 8, 12, 16, 20, or 24 mil thick.

The laminated sheet can be cut into a plurality of devices using a stamp-type cutter, or by rotary die cutting, both techniques known to one of ordinary skill in the art. Embodiments of devices of the invention can be in the shape of rectangles ("strips"), circles, circular sectors, and other regular or irregular shapes such as fanciful shapes. A device can have an area of from 1–20 $cm^2$, for example, 1–5 $cm^2$, preferably 1–2 $cm^2$, for example, 1.1, 1.3, or 1.5 $cm^2$.

An embodiment of the device of the invention that is a rigid patch can be fabricated by forming a solution or suspension of the ingredients, and laminating the solution or suspension on a solid surface, for example, a surface of a polystyrene material. After drying to remove the solvent, the film is removed and cut into the desired shapes.

EXAMPLES

Examples 1–6

Flexible Disks for Treatment of Erectile Dysfunction

A patch was manufactured by mixing solubilizer polyethylene glycol (PEG 400), a drug (prostaglandin E1) and a permeation enhancer (isopropyl myristate) under vigorous agitation to a mixture of polyvinyl pyrrolidone (PVP) in ethanol. The mixture thus obtained was coated on a siliconized polyester film and oven dried at 70° C. for 15 minutes to form what is referred to here as "a system." The system was laminated on a polyethylene backing film, and patches of 1–20 $cm^2$, for example, 1–5 $cm^2$, preferably 1.3 $cm^2$, were formed. In this example, the drug load was 0.5 mg/$cm^2$. In vitro dissolution tests of the proposed formulations using US Pharmacopoeia No 23 methodology (apparatus 5) showed that the entire amount of the drug was dissolved within 30 min.

Compositions that are embodiments of the invention containing prostaglandin E1 (PGE1) in Examples 1–6 are shown in Table 1.

Examples 7–8

Rigid Patch for Treatment of Erectile Dysfunction

The systems having a formulation for Examples 7–8 shown in Table 1 are manufactured, and may be applied to a pre-wetted area of penile skin. In Example 7, the PVP content is 91.00%, and that of PEG 400 is 3.00%, each on a dry weight basis. Alternatively, a formulation having the components of a Gliadin mixture (93.30% dry weight) and Montane 80 VGA (5.00 dry weight) can be used in this embodiment of the invention, as shown in Example 8.

Example 9

Determination of Permeation of the Components into Human Stratum Corneum

To evaluate the permeability of the formulations disclosed by the present invention, a formulation containing prostaglandin E1, 7%, Eutanol G16S, 2.5%, PVP, 43.73%, and PEG 400, 46.77%, each on a dry weight basis, was prepared by the method described above. The transdermal absorption (flux) of prostaglandin from the formulation was determined in vitro using human cadaver skin according to the procedure of Franz (J. Invest. Derm. 64, 190–105, 1975. Percutaneous absorption on the relevance of the in vitro data). The stratum corneum used in this example was obtained from fresh post-mortem skin, which was separated according to the method of Kligman et al. (Arch. Derm. 88, 702, 1963. Preparation of the isolated sheets of the human stratum corneum).

The cumulative amount of prostaglandin permeated into the stratum corneum per unit area at each time point is shown in FIG. 1. The results show that prostaglandin permeated the stratum corneum in a high amount within the first 30 min. These data indicate that an effective amount of the drug can be delivered to the site of action in a simple, safe, efficacious and timely manner, overcoming the deficiencies of systems described in the prior art.

TABLE 1

Formulations of Examples 1–8

| component | quantity (% amount on a dry basis) | | | | | | | |
|---|---|---|---|---|---|---|---|---|
| | Ex. 1 | Ex. 2 | Ex. 3 | Ex. 4 | Ex. 5 | Ex. 6 | Ex. 7 | Ex. 8 |
| PGE1[1] | 6.20 | 6.20 | 6.20 | 6.20 | 6.20 | 6.20 | 1.00 | 0.50 |
| Linoleic acid[2] | 6.00 | | | | | | | |
| Lipocol-12[3] | | 8.00 | | | | | | |
| Isopropyl myristate | | | 4.00 | | | | | |
| Glycerol monooleate | | | | 2.50 | | | | |
| Phentolamine[4] (base) | | | | | | 2.50 | | |
| Eutanol G16S[5] | | | | | 2.50 | | 2.50 | |
| L-Menthol[6] | | | | | 6.00 | 6.00 | | |
| Montane 80 VGA[7] | | | | | | | | 5.00 |
| Gliadin mixture[8] | | | | | | | | 93.30 |
| PVP[9] | 42.40 | 41.50 | 43.39 | 44.11 | 41.70 | 42.90 | 91.00 | |
| PEG 400[10] | 45.40 | 44.30 | 46.41 | 47.19 | 44.60 | 45.90 | 3.00 | |

[1]PGE1 is Prostaglandin 1 USP supplied by Bolder Ltd. (P.O. Box OH 1001 Boole, Switzerland)
[2]Linoleic acid is a fatty acid supplied by Croda Chemicals ltd. (Cowick Hull Snaith Goole, North Humberside DN 14 9AA England)
[3]Lipocol-12 is 12 mole polyethylene glycol ether of lauryl alcohol, supplied by LIPO Chemicals, Inc. (207 19th Avenue, Paterson, NJ 07540, USA)
[4]Phentolamine base is supplied as phentolamine mesylate USP 23 by Welding Crabb & Co. (Post box 30 58 40. D 20318 Hamburg, Germany), which is chemically converted to the phentolamine base
[5]Eutanol G16S is hexyldecyl stearate supplied by Henkel KGaA (Cospha 10-40191 Dusseldorf, Germany)
[6]L-Menthol is supplied by Sigma Chemical Co (P.O. Box 14508, St. Louis, MO 63178 USA)
[7]Montane 80 VGA is polysorbate monoleate supplied by Seppic (BP 228-81105 Castres Cedex, France)
[8]Gliadin mixture is obtained from Inocosm Lab. (45 Chemin de la Justice, 92290, Chatenay-Malabry, France)
[9]PVP (Kollidon 90 s) is polyvinyl pyrrolidone supplied by BASF Aktiengesellschaft (67056 Ludwigshafen, Germany)
[10]PEG 400 is polyethylene glycol supplied by ICI Surfactants (P.O. Box No90, Wilton Middlesbrough, Cleveland TS90 8JA England)

What is claimed is:

1. A delivery device for treatment of erectile dysfunction in a patient, comprising a disk, wherein the disk is made of a mixture of materials comprising a filmogenic polymer and an effective dose of a therapeutic agent suitable for treating erectile dysfunction, wherein the device does not comprise a backing layer, wherein the device does not comprise a release liner, and wherein the therapeutic agent is misoprostol.

2. The delivery device of claim 1, wherein the filmogenic polymer is selected from the group consisting of a synthetic polymer, a semi-synthetic polymer, and a naturally occurring polymer.

3. The delivery device of claim 1, wherein the disk further comprises a plasticizer in an amount of less than 30 wt %.

4. The delivery device of claim 3, wherein the plasticizer is a polyethylene glycol (PEG).

5. The delivery device of claim 4, wherein the polyethylene glycol is PEG 400.

6. The delivery device of claim 1, wherein the delivery device is a transdermal device.

7. The delivery device of claim 1, wherein the delivery device is a transmucosal device.

8. A delivery device for treatment of erectile dysfunction in a patient, comprising a disk, wherein the disk is made of a mixture of materials comprising a filmogenic polymer and an effective dose of a therapeutic agent suitable for treating erectile dysfunction, wherein the device does not comprise a backing layer, wherein the device does not comprise a release liner, wherein the filmogenic polymer is selected from the group consisting of a synthetic polymer, a semi-synthetic polymer, and a naturally occurring polymer, and wherein the disk comprises 70 to 95 wt % filmogenic polymer.

9. The delivery device of claim 8, wherein the filmogenic polymer is polyvinyl pyrrolidone.

10. The delivery device of claim 8, wherein the filmogenic polymer is gliadin.

11. The delivery device of claim 8, wherein the therapeutic agent is selected from the group consisting of a vasodilator, a smooth muscle relaxant, an anti-depressant, a parasympathetic stimulator, a renin-angiotensin system inhibitor, a local anesthetic, an ∝-blocker, and a calcium channel blocker.

12. The delivery device of claim 8, wherein the therapeutic agent is selected from the group consisting of prostaglandin, a testosterone, a yohimbine, a pentoxifylline, a trazodone, an apomorphine, a sildenafil, aminoxidil, a misoprostol, a papaverine, a nitroglycerin, a phentolamine, a moxisylyte, a linsidomine, a linear peptide, a cyclic peptide, and a pyridylguanidine compound.

13. The delivery device of claim 8, wherein the therapeutic agent is a prostaglandin.

14. The delivery device of claim 13, wherein the therapeutic agent is prostaglandin E1.

15. A delivery device for the treatment of erectile dysfunction in a patient, comprising a disk, wherein the disk is made or a mixture of materials comprising a filmogenic polymer and an effective dose of a therapeutic agent suitable for treating erectile dysfunction, wherein the disk comprises 70 to 95 wt % filmogenic polymer.

16. The delivery device of claim 15, wherein the filmogenic polymer is selected from the group consisting of a synthetic polymer, a semi-synthetic polymer, and a naturally occurring polymer.

17. The delivery device of claim 15, wherein the filmogenic polymer is polyvinyl pyrrolidone.

18. The delivery device of claim 15, wherein the therapeutic agent is misoprostol.

19. The delivery device or claim 15, wherein the therapeutic agent is a prostaglandin.

20. The delivery device of claim 19, wherein the prostaglandin is prostaglandin E1.

21. The delivery device of claim 15, wherein the mixture of materials further comprises a plasticizer in an amount of less than 30 wt %.

22. The delivery device of claim 21, wherein the plasticizer is a polyethylene glycol (PEG).

23. The delivery device of claim 22, wherein the polyethylene glycol is PEG 400.

24. The delivery device of claim 15, wherein the delivery device is a transdermal device.

25. The delivery device of claim 15, wherein the delivery device is a transmucosal device.

26. The delivery device of claim 15, wherein the therapeutic agent is selected from the group consisting of a vasodilator, a smooth muscle relaxant, an anti-depressant, a parasympathetic stimulator, a renin-angiotensin system inhibitor, a local anesthetic, an ∝-blocker, and a calcium channel blocker.

27. The delivery device of claim 15, wherein the therapeutic agent is selected from the group consisting of prostaglandin, a testosterone, a yohimbine, a pentoxifylline, a trazodone, an apomorphine, a sildenafil, aminoxidil, a misoprostol, a papaverine, a nitroglycerin, a phentolamine, a moxisylyte, a linsidomine, a linear peptide, a cyclic peptide, and a pyridylguanidine compound.

28. A delivery device for the treatment of erectile dysfunction in a patient, comprising a disk, wherein the disk is made of a mixture of materials comprising 90 to 95 wt % polyvinyl pyrrolidone and an effective dose of a therapeutic agent suitable for treating erectile dysfunction.

29. The delivery device of claim 28, wherein the therapeutic agent is selected from the group consisting of a vasodilator, a smooth muscle relaxant, an anti-depressant, a parasympathetic stimulator, a renin-angiotensin system inhibitor, a local anesthetic, an ∝-blocker, and a calcium channel blocker.

30. The delivery device of claim 28, wherein the therapeutic agent is selected from the group consisting of prostaglandin, a testosterone, a yohimbine, a pentoxifylline, a trazodone, an apomorphine, a sildenafil, aminoxidil, a misoprostol, a papaverine, a nitroglycerin, a phentolamine, a moxisylyte, a linsidomine, a linear peptide, a cyclic peptide, and a pyridylguanidine compound.

31. The delivery device of claim 28, wherein the therapeutic agent is misoprostol.

32. The delivery device of claim 28, wherein the therapeutic agent is a prostaglandin.

33. The delivery device of claim 32, wherein the prostaglandin is prostaglandin E1.

34. The delivery device of claim 28, wherein the mixture of materials further comprises a plasticizer.

35. The delivery device of claim 34, wherein the plasticizer is a polyethylene glycol (PEG).

36. The delivery device of claim 35, wherein the polyethylene glycol is PEG 400.

37. The delivery device of claim 28, wherein the delivery device is a transdermal device.

38. The delivery device of claim 28, wherein the delivery device is a transmucosal device.

39. A delivery device for the treatment of erectile dysfunction in a patient, comprising a disk, wherein the disk is made of a mixture of materials comprising 90 to 95 wt % polyvinyl pyrrolidone, an effective dose of a therapeutic agent suitable for treating erectile dysfunction and a plasticizer, wherein the device does not comprise a backing layer and wherein the device does not comprise a release liner.

40. The delivery device of claim 39, wherein the therapeutic agent is misoprostol and the plasticizer is PEG 400.

41. The delivery device of claim 39, wherein the therapeutic agent is a prostaglandin.

42. The delivery device of claim 41, wherein the prostaglandin is prostaglandin E1.

43. The delivery device of claim 39, wherein the therapeutic agent is selected from the group consisting of prostaglandin, a testosterone, a yohimbine, a pentoxifylline, a trazodone, an apomorphine, a sildenafil, aminoxidil, a misoprostol, a papaverine, a nitroglycerin, a phentolamine, a moxisylyte, a linsidomine, a linear peptide, a cyclic peptide, and a pyridylguanidine compound.

44. The delivery device of claim 39, wherein the therapeutic agent is selected from the group consisting of a vasodilator, a smooth muscle relaxant, an anti-depressant, a parasympathetic stimulator, a renin-angiotensin system inhibitor, a local anesthetic, an ∝-blocker, and a calcium channel blocker.

45. A delivery device for the treatment of erectile dysfunction in a patient, comprising a disk; wherein the disk is made of a mixture of materials comprising 70 to 95 wt % filmogenic polymer, an effective dose of a therapeutic agent suitable for treating erectile dysfunction, and at least one additive selected from the group consisting of a stabilizer, a solubilizer, and enhancer and a plasticizer.

46. The delivery device of claim 45, wherein the at least one additive comprises an enhancer selected from the group consisting of a glycolipid, a non-esterified fatty acid, an aliphatic alcohol, a fatty acid ester of an aliphatic alcohol, a cyclohexanol, a fatty acid ester of glycerol, a glycol, an aliphatic alcohol ether of a glycol, and a surfactant.

47. The delivery device of claim 45, wherein the therapeutic agent is a prostaglandin.

48. The delivery device of claim 47, wherein the prostaglandin is prostaglandin E1.

49. The delivery device of claim 47, wherein the at least one additive comprises a plasticizer.

50. The delivery device of claim 49, wherein the plasticizer is a polyethylene glycol.

51. The delivery device of claim 45, wherein the filmogenic polymer is selected from the group consisting of a synthetic polymer, a semi-synthetic polymer, and a naturally occurring polymer.

52. The delivery device of claim 45, wherein the therapeutic agent is selected from the group consisting of prostaglandin, a testosterone, a yohimbine, a pentoxifylline, a trazodone, an apomorphine, a sildenafil, a minoxidil, a misoprostol, a papaverine, a nitroglycerin, a phentolamine, a moxisylyte, a linsidomine, a linear peptide, a cyclic peptide, and a pyridylguanidine compound.

53. The delivery device of claim 45, wherein the therapeutic agent is selected from the group consisting of a vasodilator, a smooth muscle relaxant, an anti-depressant, a parasympathetic stimulator, a renin-angiotensin system inhibitor, a local anesthetic, an $\alpha$-blocker, and a calcium channel blocker.

54. A method of treating erectile dysfunction, comprising:
   selecting a device comprising a disk, wherein the disk is made of a mixture of materials comprising a filmogenic polymer and an effective dose of a therapeutic agent suitable for treating erectile dysfunction, wherein the disk comprises 70 to 95 wt % filmogenic polymer, wherein the device does not comprise a backing layer and wherein the device does not comprise a release liner;
   wetting a penile surface; and
   placing the device in contact with the wetted surface, thereby wetting the disk and delivering the at least one therapeutic agent to the penile surface in a time period that is desirable to obtain a positive response.

55. The method according to claim 54, wherein the therapeutic agent is selected from the group consisting of a vasodilator, a smooth muscle relaxant, an anti-depressant, a parasympathetic stimulator, a renin-angiotensin system inhibitor, a local anesthetic, an $\alpha$-blocker, and a calcium channel blocker.

56. The method according to claim 54, wherein the therapeutic agent is selected from the group consisting of a prostaglandin, a testosterone, a yohimbine, a pentoxifylline, a trazodone, an apomorphine, a sildenafil, aminoxidil, a misoprostol, a papaverine, a nitroglycerin, a phentolamine, a moxisylyte, a linsidomine, a linear peptide, a cyclic peptide, and a pyridylguanidine compound.

57. The method according to claim 54, wherein the therapeutic agent is present in a range of 0.1–15 wt %.

58. The method according to claim 56, wherein the therapeutic agent is misoprostol.

59. The method according to claim 54, wherein the plasticizer is present in an amount that is less than 30 wt %.

60. The method according to claim 59, wherein the plasticizer is a polyethylene glycol (PEG).

61. The method according to claim 60, wherein the polyethylene glycol is PEG 400.

62. The method according to claim 54, wherein the filmogenic polymer is a synthetic polymer.

63. The method according to claim 62, wherein the synthetic polymer is polyvinyl pyrrolidone.

64. The delivery device of claim 54, wherein the filmogenic polymer is a naturally occurring polymer.

65. The method according to claim 64, wherein the filmogenic polymer is a plant protein.

66. The method according to claim 65, wherein the plant protein is a prolamine.

67. The method according to claim 66, wherein the prolamine is a gliadin.

68. The method according to claim 54, wherein the time period is 5–100 minutes.

69. The method according to claim 68, wherein the time period is 30–60 minutes.

70. The method according to claim 54, wherein the penile surface is selected from the group consisting of (a) the shaft, (b) the glans and (c) both the shaft and the glans.

71. A method of treating erectile dysfunction, comprising:
   selecting a device comprising a disk, wherein the disk is made of a mixture of materials, wherein the disk is made of a mixture of materials comprising 90 to 95 wt % polyvinyl pyrrolidone, polyethylene glycol and an effective dose of misoprostol suitable for treating erectile dysfunction;
   wetting a penile surface; and
   placing the device in contact with the wetted surface, thereby wetting the disk and delivering the at least one therapeutic agent to the penile surface in a time period that is desirable to obtain a positive response.

72. The method according to claim 71, wherein the penile surface is selected from the group consisting of (a) the shaft, (b) the glans and (c) both the shaft and the glans.

* * * * *